United States Patent [19]

Barach et al.

[11] 4,294,930

[45] Oct. 13, 1981

[54] PROCESS FOR IMPROVING THE RECOVERY OF MICROBIAL CELL BIOMASS

[75] Inventors: Jeffrey T. Barach; Leslie Bluhm, both of Elkhart, Ind.

[73] Assignee: Miles Laboratories, Inc., Elkhart, Ind.

[21] Appl. No.: 68,876

[22] Filed: Aug. 22, 1979

[51] Int. Cl.³ ............................................. C12N 1/02
[52] U.S. Cl. ..................... 435/261; 435/243; 435/253; 435/853; 435/856; 435/857; 435/885; 426/36; 426/43
[58] Field of Search .............. 426/34, 42, 43, 36, 426/60–62; 435/261, 139, 856, 253, 243, 885, 853, 857

[56] References Cited

U.S. PATENT DOCUMENTS

| | | | |
|---|---|---|---|
| 2,397,436 | 3/1946 | Rosenqvist | 435/261 X |
| 2,472,419 | 6/1949 | Green | 435/261 |
| 2,838,443 | 6/1958 | Gillespie | 426/43 |
| 2,960,445 | 11/1960 | Wickerham | 435/261 X |
| 3,738,488 | 6/1973 | Hondermark | 435/261 X |
| 3,950,224 | 4/1976 | Ward et al. | 435/261 X |
| 4,053,642 | 10/1977 | Hup et al. | 426/43 X |
| 4,115,199 | 9/1978 | Porubcan et al. | 426/36 X |

FOREIGN PATENT DOCUMENTS

| | | | |
|---|---|---|---|
| 854695 | of 1970 | Canada | 435/261 |
| 539541 | of 1941 | United Kingdom | 435/261 |
| 761278 | of 1956 | United Kingdom | 435/261 |
| 1433328 | of 1976 | United Kingdom | 435/261 |

*Primary Examiner*—R. B. Penland
*Attorney, Agent, or Firm*—Louis E. Davidson

[57] ABSTRACT

A process is provided for improving the recovery of microbial cell biomass, which includes the steps of subjecting a culture broth containing chain-forming microorganisms to shearing conditions sufficient to shorten the chain-length of microbial cells whereby the packed cell volume of the cell biomass is substantially reduced and then recovering the thus treated biomass from the broth by centrifugation.

4 Claims, No Drawings

PROCESS FOR IMPROVING THE RECOVERY OF MICROBIAL CELL BIOMASS

BACKGROUND AND PRIOR ART

The manufacture of many fermented food products, such as cheese, buttermilk, sour cream, yoghurt and the like, requires the use of starter cultures, i.e. a concentrated microbial biomass, as described in U.S. Pat. Nos. 3,159,490 and 4,115,199. These starter cultures can be prepared by a well-known method which involves culturing the microorganism in a nutrient broth to produce a desired cell population and then recovering the cell biomass from the broth by centrifugation (J. of the Society of Dairy Technology 30, 36[1977]). To facilitate handling and sample uniformity, it is desirable that the recovered biomass having an effective microbial cell population, usually greater than about $1.0 \times 10^8$ colony forming units (CFU)/ml, be contained in a packed cell volume of less than about 5% on a volume/volume basis based on the total volume of the culture broth.

Some types of microorganisms, however, which grow in long filaments or chains of cells, for example about 15 to 30 cells in length, form a loosely packed or flocculant biomass which is difficult to concentrate and inefficient to recover by centrifugation. This flocculant biomass inefficiently fills the holding area of the centrifuge thus resulting in considerable loss of the biomass to the effluent stream and reducing the yield of the recovered biomass.

SUMMARY OF THE INVENTION

In accordance with the present invention, a novel process for recovering chain-forming microorganisms from a culture broth with improved yield is provided comprising subjecting a culture broth containing chain-forming microorganisms to shearing conditions sufficient to shorten the chain length of said microorganisms and thereby substantially reduce the packed cell volume thereof, and then recovering said microorganisms from said culture broth.

DETAILED DESCRIPTION OF THE INVENTION

The culture broths which are most suitably treated by this process contain microorganisms which grow in long filaments or chains of cells, for example 10 or 30 or more cells in length, and form a loosely packed or flocculant biomass upon centrifugation. Such microorganisms include chain-forming lactic acid-producing microbes. Representative microorganisms include *Streptococcus cremoris*, *Streptococcus lactis*, *Streptococcus diacetylactis*, *Streptococcus thermophilus*, *Lactobacillus bulgaricus*, *Lactobacillus helveticus*, *Lactobacillus casei*, *Lactobacillus plantarium*, mixed cultures thereof and the like. These culture broths are prepared by well-known methods which involve culturing the microorganism in a nutrient broth under suitable conditions until a desired cell population is obtained.

In practicing this invention in a continuous, semicontinuous or batch mode, the culture broth containing such chain-forming microorganisms is subjected to shear conditions sufficient to shorten the chain-length of microorganisms whereby the packed cell volume of the cell biomass of microorganisms prior to recovery is substantially lower than the packed cell volume obtainable without the benefit of this shearing treatment under similar conditions. Preferably the packed cell volume before recovery by centrifugation will be less than about 5% on a volume/volume basis based upon the total volume of the culture broth. Suitable means for shearing the culture broth include the use of high speed dispersers, homogenizers, sonic oscillators and the like. The shear conditions preferably should be regulated to obtain a maximum reduction in packed cell volume with a minimum loss of cell viability, metabolic activity and biomass stability. These shearing conditions can be readily determined by one skilled in the art without undue experimentation. The thus-treated culture broth is then centrifuged to recover the cell biomass from the broth. Due to the substantially reduced packed cell volume, the recovered biomass is obtained in greater yield, is easier to handle and to transport and is more consistently uniform. The recovered biomass is still useful in well-known processes for production of fermented food products.

Packed cell volume can be determined by the following procedure. Ten milliliters of a biomass-containing sample prior to recovery is put into a graduated centrifugal tube. The tube containing the sample is then placed in a centrifuge and spun at $5130 \times G$ for 10 minutes. The volume of the sediment ($V_s$) and the total volume ($V_t$) are measured. The packed cell volume (%) is represented by the expression $100\, V_s/V_t$.

The following examples further illustrate the present invention and are not intended to limit the breadth described above.

EXAMPLE I

This example illustrates the application of this invention to improve the recovery of a biomass.

Four hundred gallons of an aqueous nutrient broth containing predigested milk protein (2.2%), lactose (3.1%), buffering salts (0.36%) and yeast extract (0.25%) was innoculated with a mixture of lactic acid-producing microbes of *Streptococcus cremoris* and *Streptococcus lactis* (used to produce Marstar ® brand blend SG-1). The innoculated broth was incubated at 22° C. for 16 hours to propagate the microorganism to a total population of $8.16 \times 10^{14}$ CFU. The pH during incubation was maintained at a value between 5.5 and 6.8 by the addition of concentrated ammomium hydroxide. The culture broth was then cooled to 10° C. and the pH was adjusted to about neutrality by the addition of concentrated ammonium hydroxide. The broth was examined microscopically and found to contain therein a large portion of long chain units of cells from about 20 to 25 cells in length. One half of the culture broth, representing a control sample, was then passed to a commercially available desludging centrifuge operated at $6000 \times G$ to recover 19.5 Kg of cell biomass.

The remaining 200 gallons of culture broth, representing a test sample, were passed through an in-line commercial homogenizer operated at about 500–550 psig and then passed directly to the commercially available desludging centrifuge operated under the same conditions for the control sample to recover 21.0 Kg of cell biomass. A portion of the broth just prior to centrifugation was examined microscopically and found to contain short chain units of cells about 4 to 6 cells in length.

Samples of the respective biomasses were taken just prior to their passage to the desludging centrifuge and the packed cell volumes thereof were measured and compared. The control had a packed cell volume of 12.0%. The test sample had a packed cell volume of 4.8%. These results clearly illustrate the substantial reduction in packed cell volume achievable by this process.

The control biomass, recovered from the desludging centrifuge, had a total population of $1.13 \times 10^{14}$ CFU. The test sample biomass, recovered from the desludging centrifuge, had a total population of $3.57 \times 10^{14}$ CFU. This represents a three fold increase in the biomass recovery over the control. These results thus illustrate a dramatic improvement in the recovery of the biomass by this process. The recovered material can then be used in well-known processes for production of fermented food products.

EXAMPLE 2

In a similar manner following the procedure as described in Example 1, microbial biomass was recovered from two culture broths containing mixtures of *Streptococcus cremoris* and *Streptococcus lactis* used to produce Marstar ® brand blends MC and LD. Samples of test biomass and control biomass were taken just prior to passage to the desludging centrifuge and the packed volumes thereof were determined and compared. The total weight and population of the test and control biomasses, after recovery, were measured and compared. The results are found in Table I below:

TABLE 1

| Sample | Packed Cell Volume | Biomass Recovered (Kg) | Population (CFU) |
|---|---|---|---|
| Control Blend MC | 11% | 19.75 | $6.32 \times 10^{14}$ |
| Test Blend MC | 4% | 20.0 | $8.6 \times 10^{14}$ |
| Control Blend LD | 8.5% | 17.5 | $6.13 \times 10^{14}$ |
| Test Blend LD | 3.2% | 15.0 | $9.75 \times 10^{14}$ |

These results clearly illustrate that the packed cell volume prior to recovery is substantially reduced and the biomass recovery or yield expressed as cell population or colony forming units is dramatically improved by the process of this invention.

EXAMPLE 3

In a similar manner, as described in Example 1, 200 gallons of nutrient broth were innoculated with a mixed strain of *Streptococcus cremoris* and *Streptococcus lactis* used to produce Marstar ® brand blend SG-1. During the final half of the incubation period, the broth was recirculated through a commercial in-line homogenizer of the disintegrator type at the rate of 2.5 gal/min until the incubation was complete. The broth was then cooled to 10° C., the pH was adjusted to a value of 6.5 and the resultant broth was passed directly to a commercial centrifuge as described in Example 1. Compared to a control without the shearing treatment, the packed cell volume of samples taken prior to recovery was reduced from about 12% to 6.8% and the recovered biomass yield based on population was increased about 1.6 fold.

What is claimed is:

1. A process for recovering chain-forming microorganisms from a culture broth with improved yield, consisting essentially of subjecting a culture broth containing chain-forming microorganisms to shearing conditions in apparatus selected from the class consisting of high speed dispersers, homogenizers and sonic oscillators sufficient to shorten the chain length of said microorganisms and thereby substantially reduce the packed cell volume thereof, and then recovering said microorganisms from said culture broth by centrifugation.

2. A process according to claim 1, wherein the packed cell volume of the sheared biomass of microorganisms prior to recovery is less than about 5% on a volume by volume basis based upon the total volume of the culture broth.

3. A process according to claim 1, wherein the microorganisms are chain-forming lactic acid producing microbes.

4. A process according to claim 1, wherein the microorganisms are selected from *Streptococcus cremoris, Streptococcus lactis, Streptococcus diacetylactis, Streptococcus thermophilus, Lactobacillus bulgaricus, Lactobacillus helveticus, Lactobacillus casei, Lactobacillus plantarium,* and mixtures thereof.

* * * * *